United States Patent [19]

Toda

[11] Patent Number: 4,785,111

[45] Date of Patent: Nov. 15, 1988

[54] N-CYCLOHEXYL-POLYCARBOXAMIDE COMPOUND AND DERIVATIVES THEREOF

[75] Inventor: Fumio Toda, Ehime, Japan

[73] Assignee: Mitsubishi Corporation, Tokyo, Japan

[21] Appl. No.: 837,199

[22] Filed: Mar. 10, 1986

[30] Foreign Application Priority Data

Mar. 9, 1985 [JP] Japan .................................. 60-46999
May 27, 1985 [JP] Japan ................................ 60-113553
May 27, 1985 [JP] Japan ................................ 60-113554
Nov. 22, 1985 [JP] Japan ................................ 60-262992

[51] Int. Cl.$^4$ .................. C07D 213/81; C07D 213/82; C07D 103/30; C07D 103/37
[52] U.S. Cl. .................................. 546/316; 546/323; 564/152; 564/153; 564/156
[58] Field of Search ............... 546/316, 323; 564/152, 564/153, 156

[56] References Cited

FOREIGN PATENT DOCUMENTS 2167201 5/1986 United Kingdom .

OTHER PUBLICATIONS

Toda et al., Chemical Abstracts 105: 78550K.
Kleiner, T. et al. Chem. Ber. 118 pp. 1071–1077 (1985).
Vögtle, F. et al. Chem. Ber. 116 pp. 2028–2034 (1983).
Advanced Organic Chemistry, Part A: Structure and Mechanisms, Francis A. Carey et al., Sect. 4.7, pp. 161–162 & 209–210.

Primary Examiner—Mary C. Lee
Assistant Examiner—Dale A. Bjorkman
Attorney, Agent, or Firm—Oblon, Fisher, Spivak, McClelland & Maier

[57] ABSTRACT

This invention provides novel N-cyclohexyl-polycarboxamide compounds having inclusion power for a variety of compounds, the N-cyclohexyl-polycarboxamide compound being of the general formula

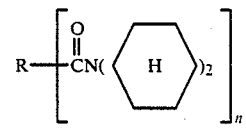

where R is a benzene ring, an ethylidene group, a benzylidene group, a 1,2-cyclohexylene group, a 1,2-cyclohexenylene-4 group, or a 2,3-, 2,5- or 2,6-pyridinediyl group, and n is equal to 2, 3 or 4 when R is a benzene ring, and equal to 2 when R is one of the aforesaid groups excluding a benzene ring. These compounds exhibit the host function of taking up a variety of compounds as guest compounds to form inclusion complexes, and can be utilized for the separation and purification thereof.

11 Claims, 7 Drawing Sheets

N-CYCLOHEXYL-POLYCARBOXAMIDE COMPOUND AND DERIVATIVES THEREOF

FIELD OF THE INVENTION

This invention relates to novel N-cyclohexyl-polycarboxamide compounds. These compounds serve as host compounds which take up a variety of solvent and other compounds, including alcohols, phenols, etc., as guest compounds to form inclusion complexes, and can be utilized for the separation and purification of such compounds.

BACKGROUND OF THE INVENTION

Starting from a study on the phenomena of crystal solvents, the present inventor has investigated host-guest complexes or inclusion complexes consisting of a specific compound (host compound) having specific molecules (guest compounds) trapped therein, and has found that, for example, 9,10-dihydroxy-9,10-dihydroanthracene, 2,5-bis(2,4-dimethylphenyl)hydroquinone, 2,5-bis(4-chlorophenyl)hydroquinone and the like have excellent inclusion power for alcohols [Chemistry Letters (The Chemical Society of Japan, 1983), pp. 1521–1524; Kagaku-Sochi (Japanese), September 1984, pp. 35–43].

On the other hand, the present inventor previously found that diacetylenediols take up various compounds to form stable crystalline complexes. For example, 1,1,6,6-tetraphenyl-hexa-2,4-diyne-1,6-diol and dimethylformamide form a 1:2 complex. On the basis of these facts, the present inventor has found the possibility that host compounds capable of taking up alcoholic compounds may be obtained by the molecular design of suitable compounds having amide linkages.

SUMMARY OF THE INVENTION

The present inventor has made extensive study in pursuit of the aforesaid possibility and has found that amide derivatives of certain policarboxylic acids have inclusion power for a wide range of compounds.

Specifically, the present invention provides novel compounds useful as host compounds, and they include N-cyclohexyl-polycarboxamide compounds of the formula

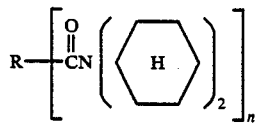

and derivatives thereof, where R is a benzene ring, an ethylidene group, a benzylidene group, a 1,2-cyclohexylene group, a 1,2-cyclohexenylene-4 group, or a 2,3-, 2,5- or 2,6-pyridinediyl group, and n is equal to 2, 3 or 4 when R is a benzene ring, and equal to 2 when R is one of the aforesaid groups excluding a benzene ring.

These compounds can be obtained by reacting the corresponding polycarboxylate esters or polycarbonyl polychlorides with dicyclohexylamine.

Various derivatives of the aforesaid compounds can be obtained by using, as starting materials, dicyclohexylamine derivatives having at least one alkyl or other side chain on the cyclohexyl group.

It has been found that the compounds of the present invention have the inclusion power to take up a wide variety of guest compounds including not only alcoholic compouonds but also aromatic hydrocarbons. When a compound of the present invention is brought into contact with a guest compound, the resulting inclusion complex can be precipitated as crystals. In order to separate the guest compound from the complex thus obtained, such technique as distillation, column chromatography, replacement by another guest, separative elution with acid or base, and the like may be used according to the difference in physical and chemical properties between the host and the guest molecules. Where the vapor pressure of the guest compound is relatively low, it is most convenient to heat and distill the complex, and the guest compound separated and recovered in this manner is highly pure. The solid freed of the guest compound can be reused as a host compound. Where the guest compound recovered by heating an inclusion complex has a high boiling point, the heating is carried out under reduced pressure.

DETAILED DESCRIPTION OF THE INVENTION

Figure 1:
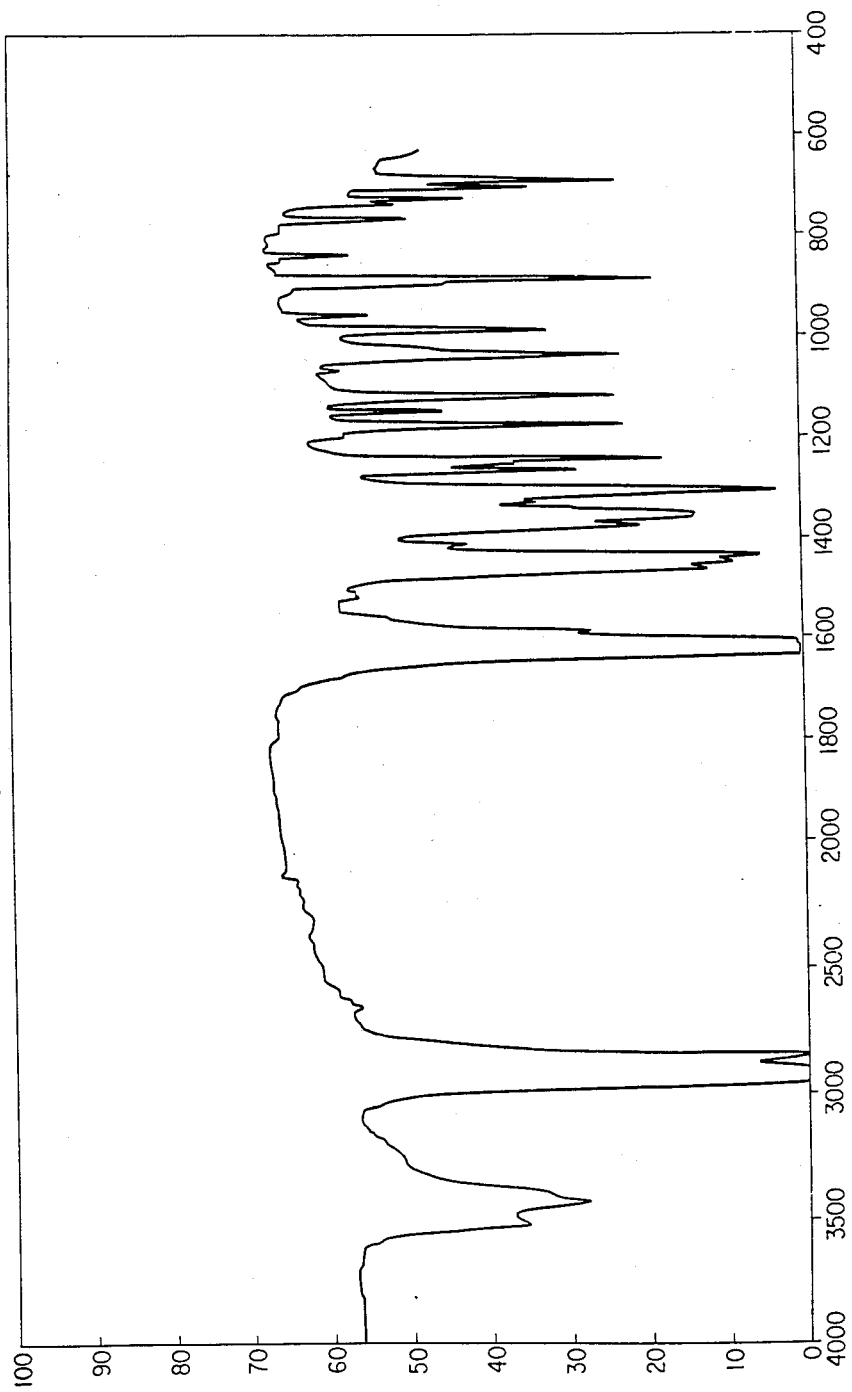
FIG. 1 is an infrared absorption spectrum of the 1:2 complex of N,N,N',N',N'',N''-hexacyclohexyl-trimesamide in accordance with the present invention and methanol.

The N-cyclohexyl-polycarboxamide compound of the present invention can be represented by the general formula

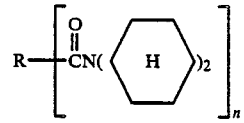

where R is a benzene ring, an ethylidene ring, a benzylidene grpoup, a 1,2-cyclohexylene group, a 1,2-cyclohexenylene-4 group, or a 2,3-, 2,5- or 2,6-pyridinediyl group, and n is equal to 2, 3 or 4 when R is a benzene ring, and equal to 2 when R is one of the aforesaid groups excluding a benzene ring.

Specific examples of the novel N-cyclohexyl-polycarboxamide compounds of the present invention represented by the above general formula include A: N,N,N',N'-tetracyclohexyl-phthalamide,
B: N,N,N',N',N'',N''-hexacylohexyl-trimesamide,
C: N,N,N',N',N'',N'',N''',N'''-octacyclohexyl-pyromellitamide,
D: N,N,N',N'-tetracyclohexyl-fumaramide,
E: N,N,N',N'-tetracyclohexyl-phenylmalonamide, F: N,N,N',N'-tetracyclohexyl-1,2-cyclohexanedicarboxamide, G: N,N,N',N'-tetracyclohexyl-cis-Δ⁴-cyclohexene-1,2-dicarboxamide, H: N,N,N',N'-tetracyclohexyl-2,6-pyridinedicarboxamide, I: N,N,N',N'-tetracyclohexyl-2,3-pyridinedicarboxamide, and J: N,N,N',N'-tetracyclohexyl-2,5-pyridinedicarboxamide, as well as derivatives of the foregoing.

The guest compounds with the compounds of the present invention can form inclusion complexes covering a wide variety of solvent compounds. Such solvent compounds include, for examples, monoalcohols such as methanol, ethanol, propanols, butanols, cyclohexanol, etc.; diols such as ethylen glycol to octandiol, etc.; aromatic compounds such as phenol, cresol, benzene, toluene, naphthalene, methylnaphthalene, etc.; organic acids and their esters such as acetic acid, benzoic acid, ethyl benzoate, etc.; and other solvent compounds such as dimethylformamide (DMF), tetrahydrofuran (THF), dioxane, dichloromethane, trichloroethane, etc.

The compounds of the present invention may be used as host compounds to form inclusion complexes with a various guest compounds. This can be accomplished simply by bringing compounds of the present invention into contact with a guest compound. If desired, such inclusion complexes can be more efficiently formed by dissolving or melting the compound of the opresent invention by the application of heat. Alternatively, the compound of the present invention may also be used in the form of a solution in a suitable solvent for which the compounds does not exhibit inclusion power.

The inclusion complex so formed can be precipitated as crystals. In order to separate the guest compound from the complex thus obtained, such techniques as distillation, column chromatography, replacement by another guest, separative elution with acid or base, and the like may be used according to the difference in physical and chemical properties between the host and the guest molecules. Where the vapor pressure of the guest compound is relatively low, it is most convenient to heat and distill the complex, and the guest compound separated and recovered in this manner is highly pure, and the solid freed of the guest compound can be reused as a host compound. Where the guest compound recovered by herating an inclusion complex has a high boiling point, the heating is carried out under reduced pressure.

Since the compounds of the present invention form stable complexes with a variety of compounds acting as guest compounds, the former compounds can be utilized for the separation and purification of the latter compounds. Moreover, even when brought into contact with analogous compounds, the compounds of the present invention form complexes with some of them, but not with the others. Accordingly, they can also be utilized for the separation of certain stereoisomers.

The present invention is further illustrated by the following examples. In these examples, the structural formulas of some typical compounds in accordance with the present invention and the procedures for the preparation thereof are described.

EXAMPLE 1

Preparation of N,N,N',N'-tetracyclohexyl-phthalamide (Compound A):

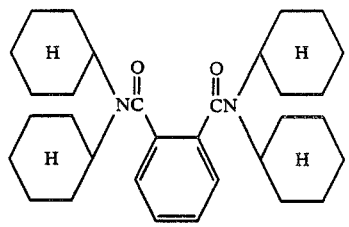

A 200-ml. pear shaped flask was charged with 33 g. of phthalic anhydride and 50 g. of phosphorus pentachloride, and shaken well. The resulting reaction mixture was refluxed in an oil bath at about 120° C. for 12 hours. After the removal of POCl₃ by distillation, the phthaloyl dichloride so formed was distilled at 10 mm.Hg and 101° C. Its yield was 26 g. (58%).

10 g. of the phthaloyl dichloride obtained in the above-described manner was dissolved in 40 ml. of benzene and the resulting solution was slowly added dropwise, with occasional shaking, to an ice-cold soluton of 38 g. of dicyclohexylamine in 40 ml. of benzene. After completion of the addition, the resulting reaction mixture was shaken well and allowed to stand for 6 hours. Compound A so formed was extracted with hot benzene and recrystallized from methanol. Thus, there was obtained a yield of 22 g. (91%) of Compound A having a melting point of 202°–204° C.

EXAMPLE 2

Preparation of N,N,N',N',N'',N''-hexacyclohexyl-trimesamide (Compound B)

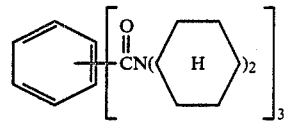

A pear shaped flask was charged with trimesic acid and phosphorus pentachloride in a molar ratio of 3:1, and shaken well. The resulting reaction mixture was heated to about 80° C. to initiate the reaction. After the reaction was almost complete, the reaction mixture was refluxed for about 2 hours. When POCl₃ was removed by distillation under reduced pressure, there was obtained an approximately 100% yield of trimesoyl trichloride in the form of a solid.

Eight moles of dicyclohexylamine was dissolved in an equal amount of benzene and placed in a three neck flask fitted with a Dimroth condenser and a dropping funnel. Also, 1 mole of the trimesoyl trichloride obtained in the above-described manner was dissolved in an equal amount of benzene and charged into the dropping funnel. At the open ends of the Dimroth condenser and the dropping funnel, a dessicating agent was provided so as to protect the reaction system from atmospheric moisture.

Figure 2:
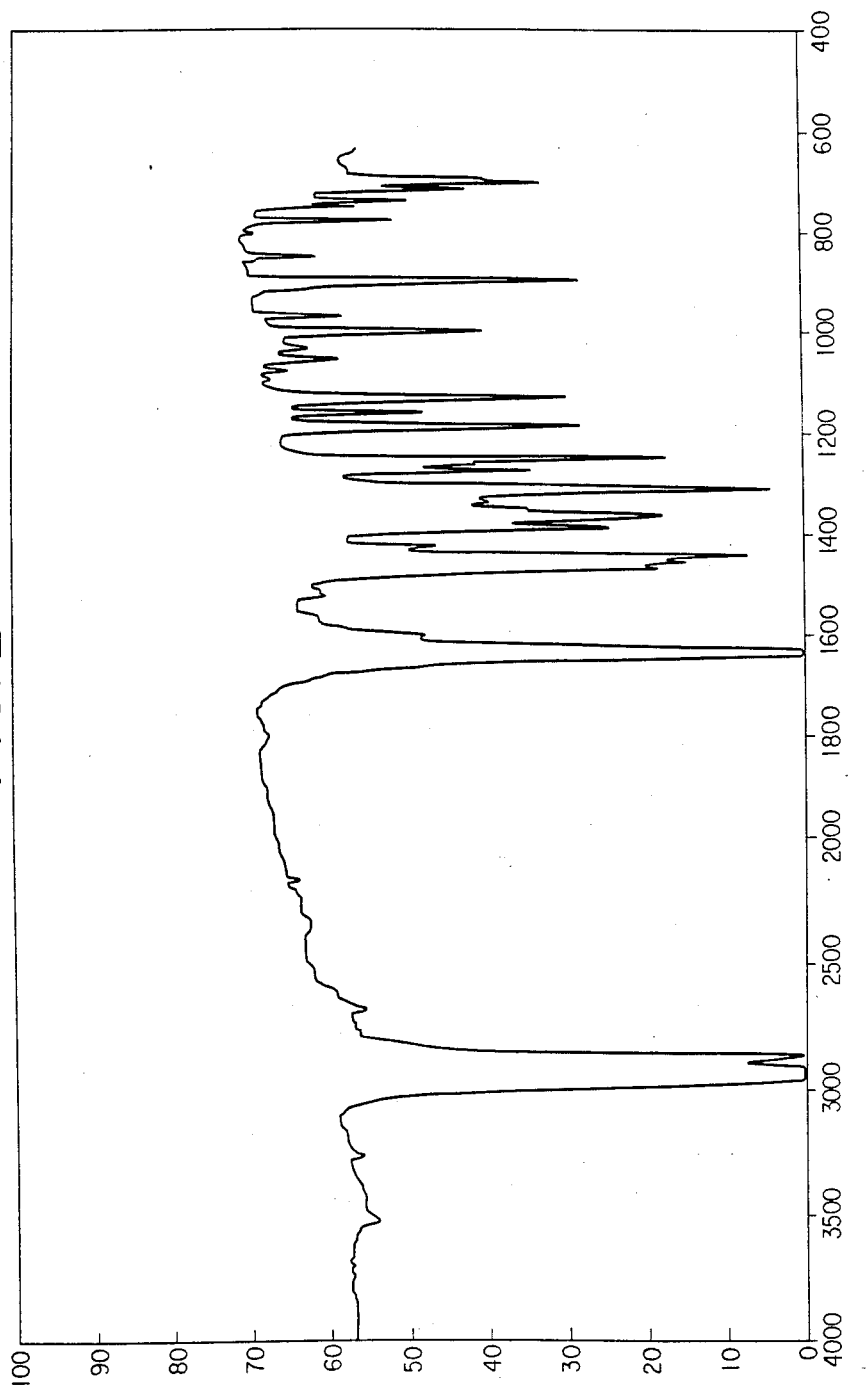
FIG. 2 is an infrared absorption spectrum of N,N,N',N',N'',N''-hexacyclohexyl-trimesamide obtained by decomposition of the aforesaid complex.

The precipitated amine hydrochloride was separated by filtration, and washed with a small amount of benzene. The filtrate was combined with the washings and the resulting mixture was heated to distill off the benzene. When the resulting residue was purified by recrystallization from methanol, the 1:2 complex of Compound B and methanol was obtained. When this complex was heated to expel the methanol, there was obtained a 75% yield of Compound B in the form of an amorphous powder. An infrared absorption spectrum of Compound B obtained by decomposition of the complex is shown in FIG. 2.

EXAMPLE 3

Preparation of N,N,N',N',N'',N'',N''',N'''-octacyclohexylpyromellitamide (Compound C)

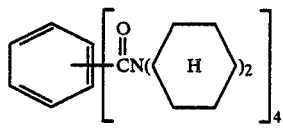

A pear shaped flask was charged with pyromellitic anhydride and phosphorus pentachloride in a molar ratio of 1:2, and shaken well. The resulting reaction mixture was worked up in the same manner as in Example 2. Thus, there was obtained an approximately 100% yield of pyromellitic tetrachloride.

Using the same apparatus as described in Example 2, the procedure of Example 2 was repeated except that the pyromellitic tetrachloride obtained in the above-described manner and dicyclohexylamine were used in a molar ratio of 1:8 and benzene or THF was used as the recrystallization solvent. Thus, there was obtained a 70% yield of Compound C.

Figure 3:
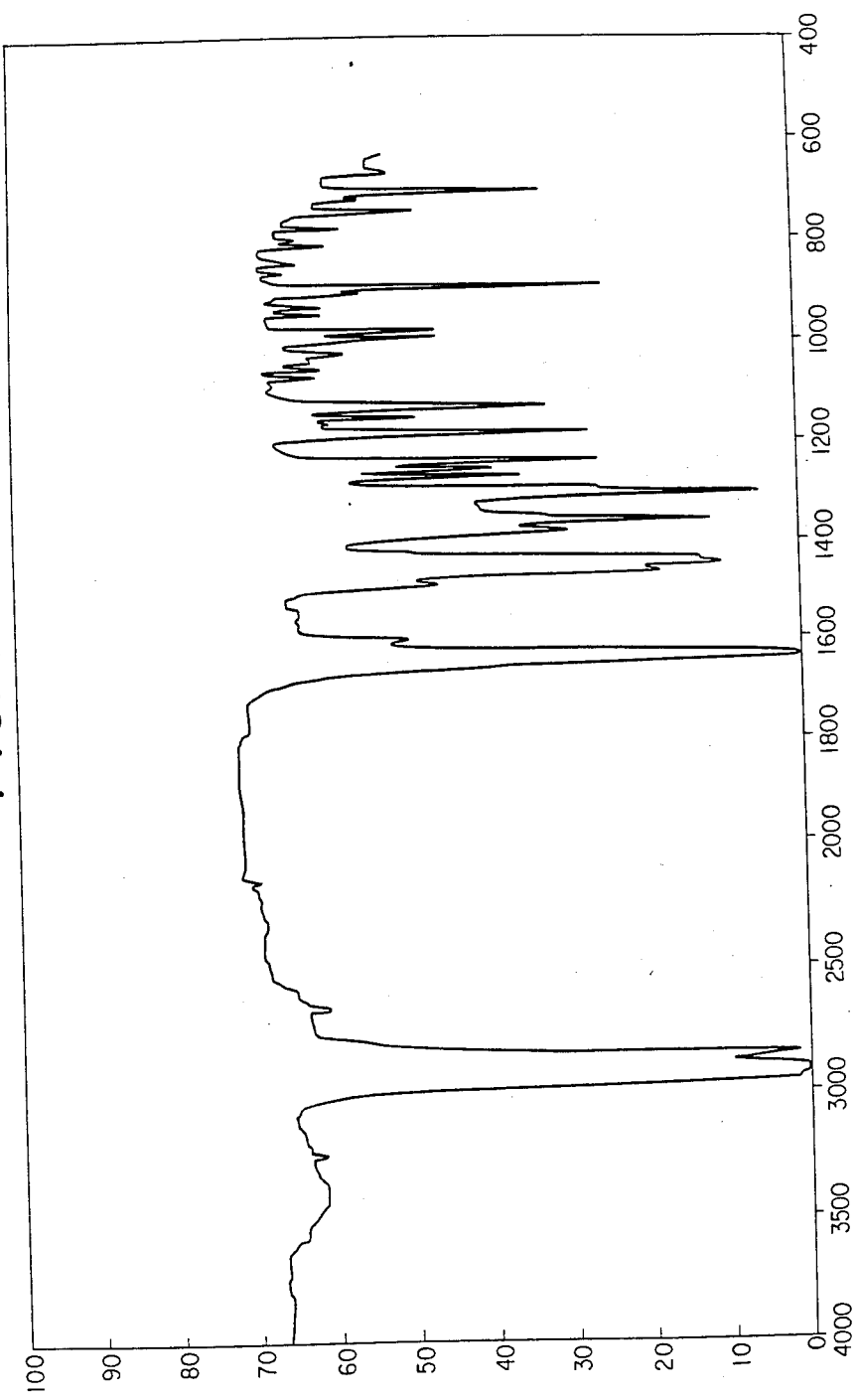
FIG. 3 is an infrared absorption spectrum of N,N,N',N',N'',N'',N''',N'''-octacyclohexyl-pyromellitamide in accordance with the present invention.

An infrared absorption spectrum of Compound C thus obtained is shown in FIG. 3.

EXAMPLE 4

Preparation of N,N,N',N'-tetracyclohexyl-fumaramide (Compound D)

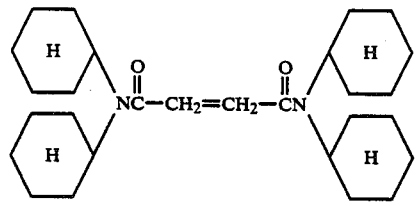

73 g. of dicyclohexylamine was placed in an Erlenmeyer flask, and 100 ml. of benzene was added thereto. Using a buret, 15.3 g. of fumaroyl dichloride was slowly added dropwise thereto with constant stirring. In order to prevent the temperature from being raised due to the evolution of heat, the reaction mixture was externally cooled with water or ice and thereby maintained at about room temperature. Upon completion of the addition, the reaction was complete and dicyclohexylamine hydrochloride precipitated.

The precipitae was separated by filtaration, and washed with a small amount of benzene. The filtrate was combined with the washings and the resulting mixture was heated to distill off the benzene. When the resulting residue was purified by recrystallization from methanol, the 1:2 complex of Compound D and methanol was obtained in the form of colorless prisms. When this crystalline product wa heated to expel the methanol, there was obtained a yield of 40 g. (95%) of Compound D in the form of an amorphous powder.

Figure 4:
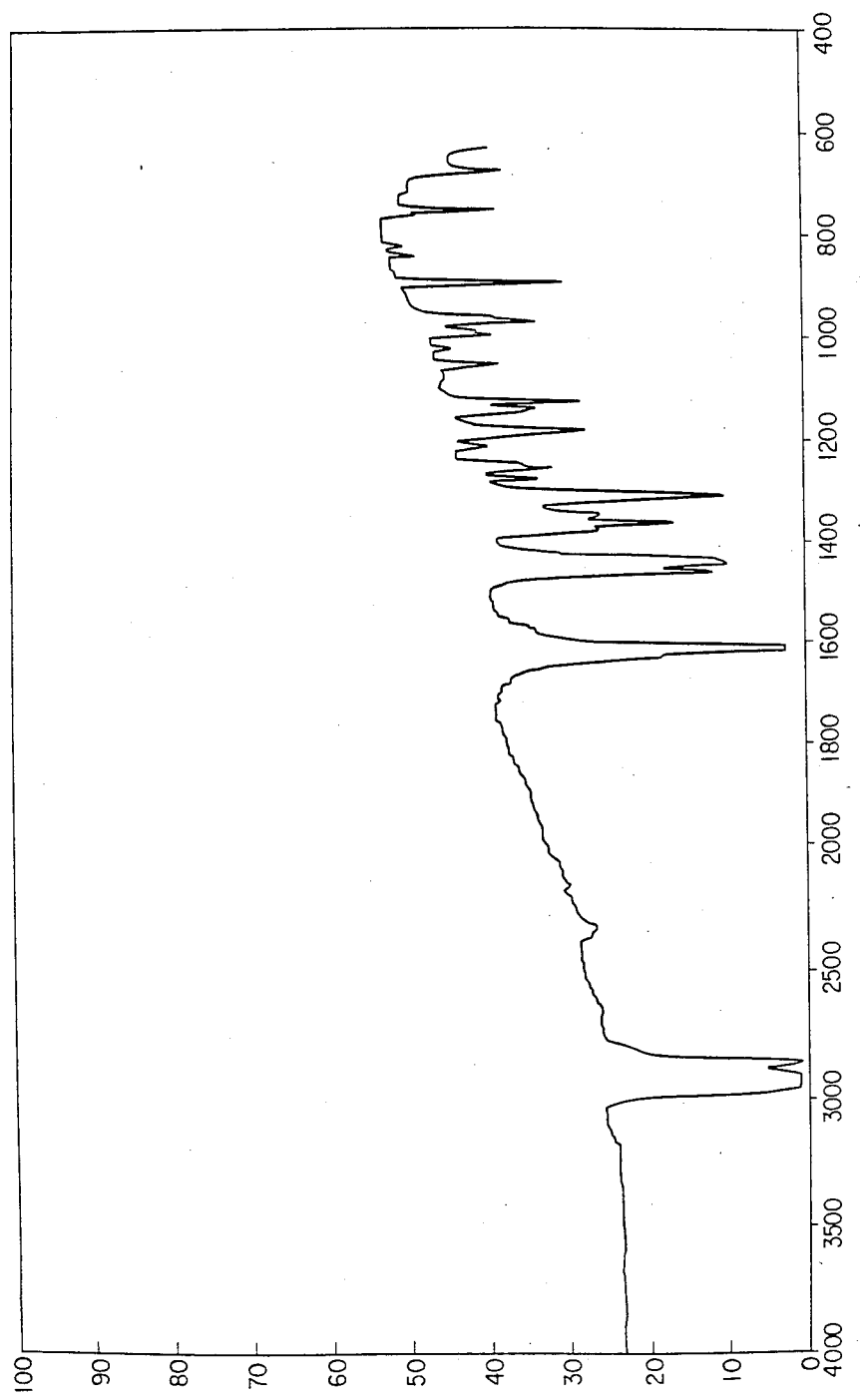
FIG. 4 is an infrared absorption spectrum of N,N,N',N'-tetracyclohexyl-fumaramide in accordance with the present invention.

Compound D has a melting point of 206°–208° C., and an infrared absorption spectrum thereof is shown in FIG. 4.

In several examples given below, Compound D was used as a host compound to separate varius guest compounds. However, it is to be understood that, since the compounds were used in small amounts, considerable losses resulted during operation and, therefore, the yield was not entirely exact and might have been underestimated.

EXAMPLE 5

Figure 5:
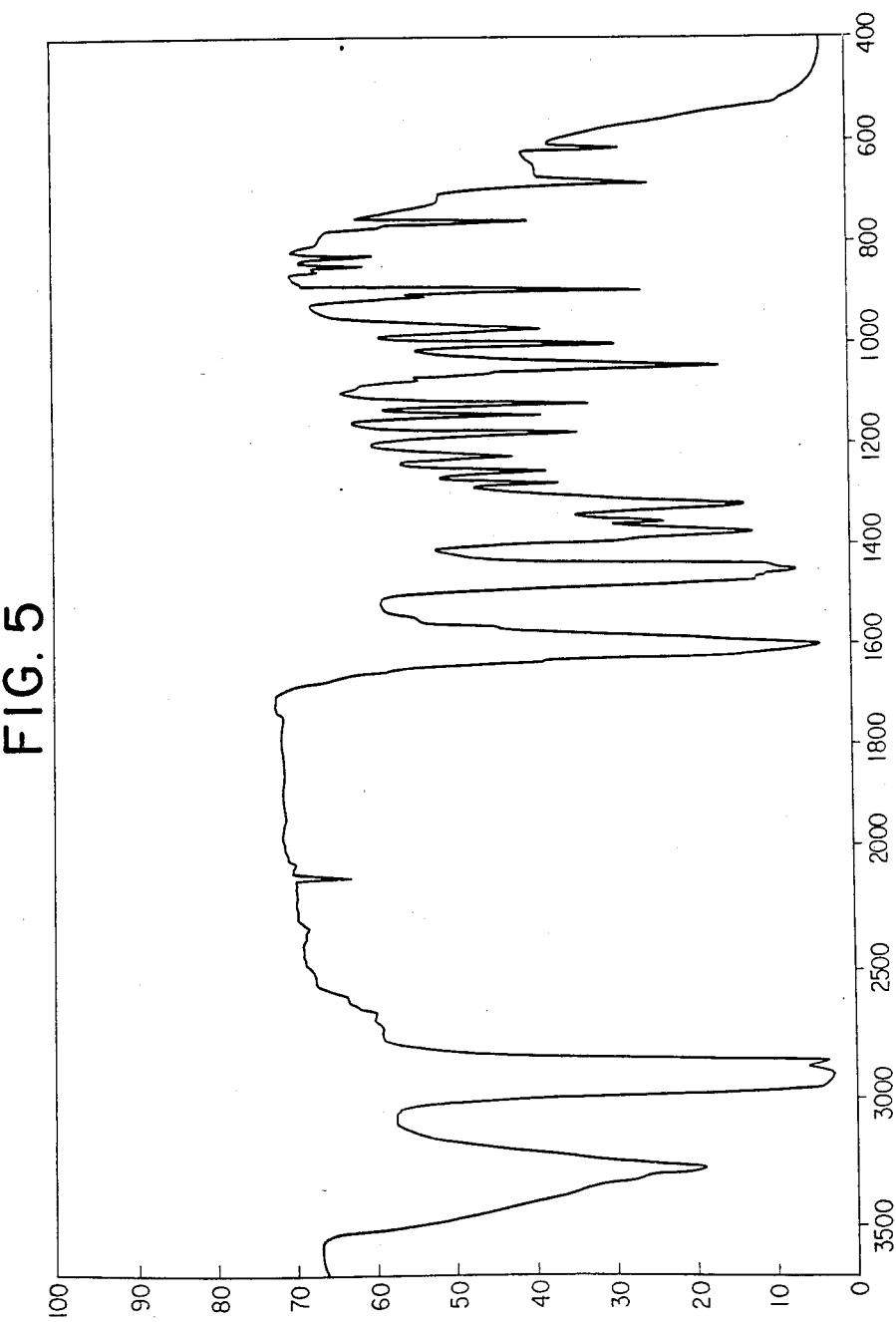
FIGS. 5 to 7 are infrared absorption spectra of the inclusion complexes formed by the addition of propargyl alcohol, 2-butyne-1,4-diol and n-butanediol, respectively, to N,N,N',N'-tetracyclohexyl-fumaramide.

2.0 g. of Compound D prepared in the above-described manner and 0.73 g. of propargyl alcohol containing 30 wt.% of water were dissolved in 3 ml. of n-butanol by the application of heat. When the resulting solution was allowed to stand at room temperature for 1 hour, 1.45 g. of colorless prisms precipitated. This crystalline product has no definite melting point, but gave an infrared absorption spectrum as shown in FIG. 5. When it was heated to 150° C., 0.27 g. of propargyl alcohol was obtained. Thus, the product was found to be the 1:2 inclusion complex of Compound D and propargyl alcohol.

EXAMPLE 6

Figure 6:
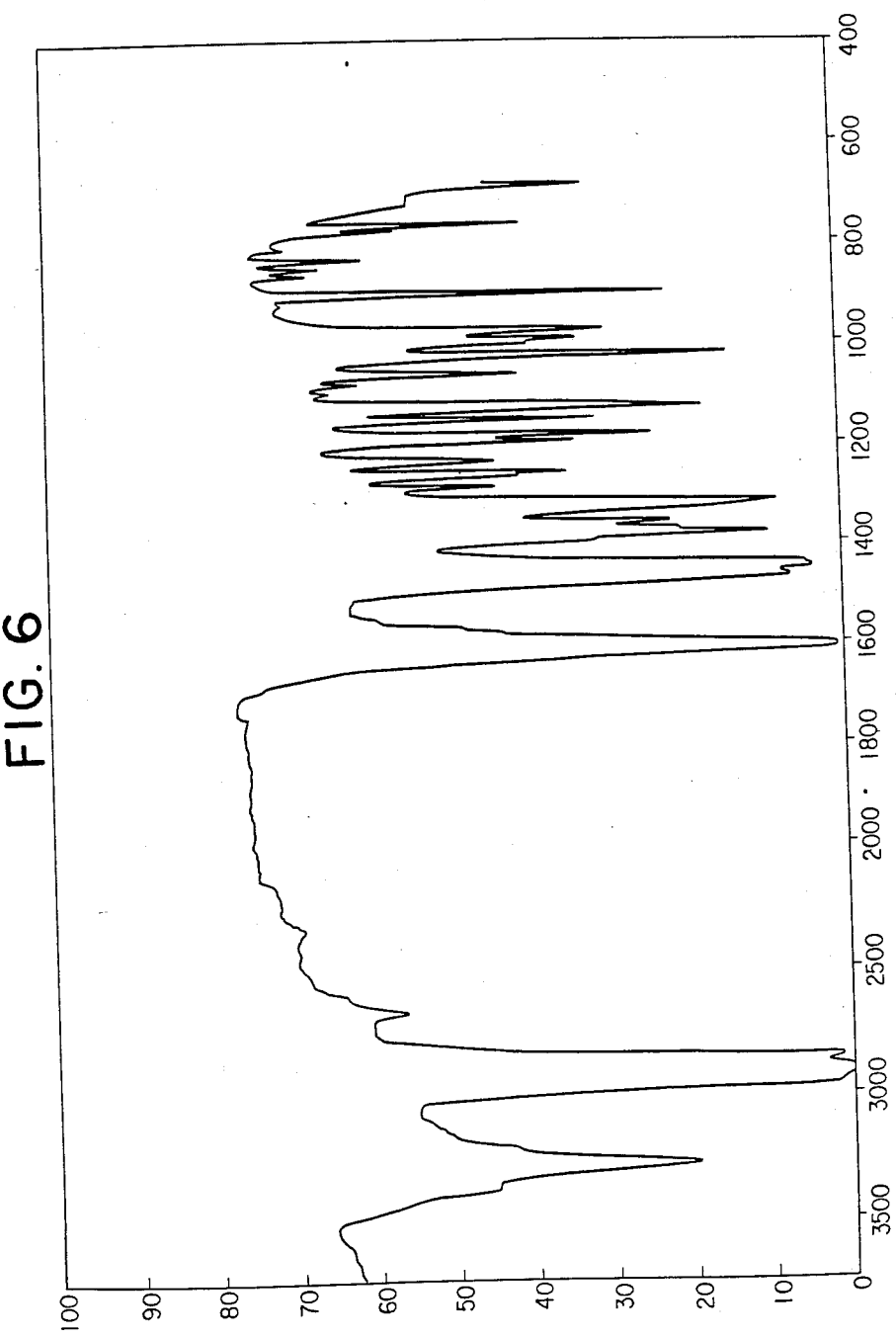
Figure 7:
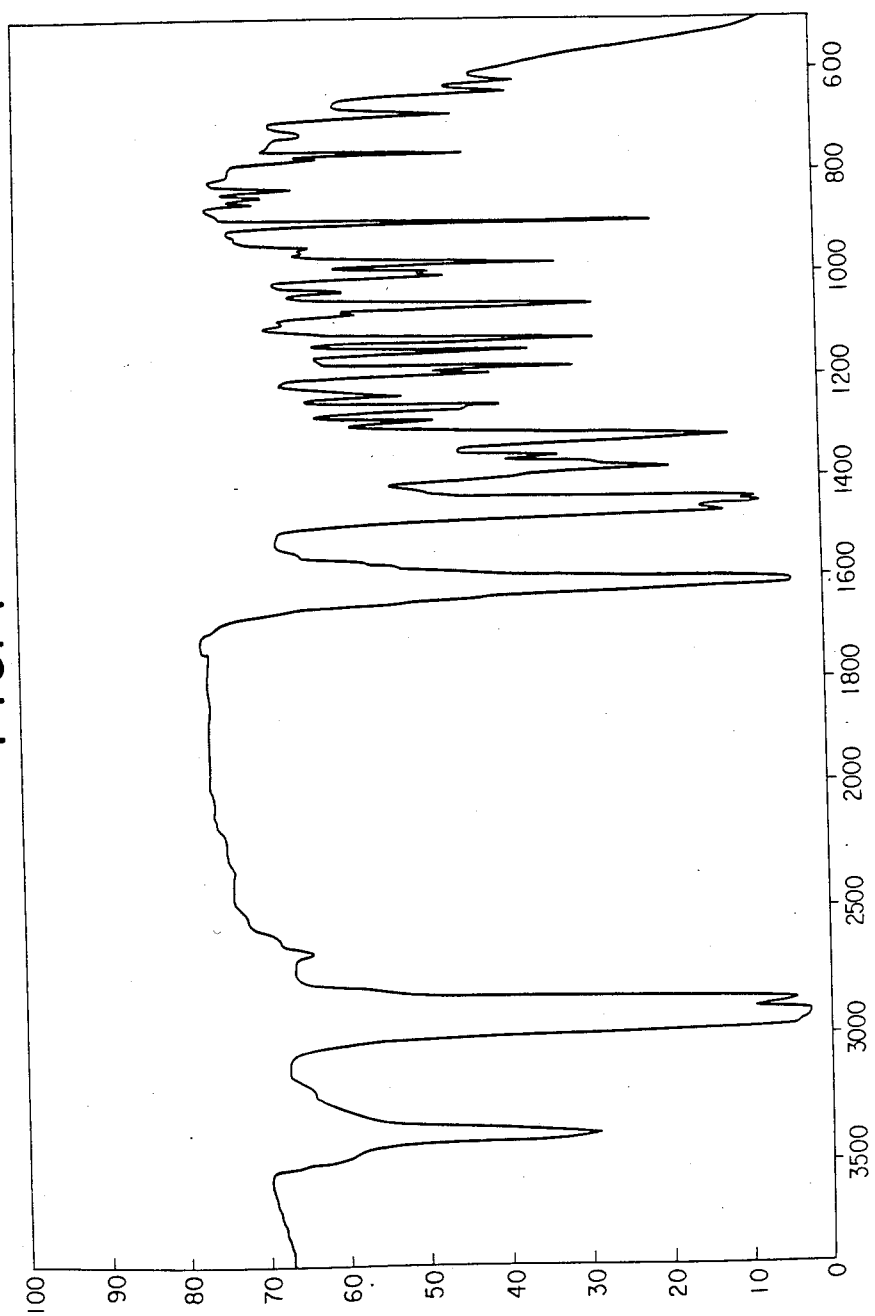

2.0 g. of Compound D and 0.58 g. of 2-butyne-1,4-diol containing 30 wt.% of water were dissolved in 5 ml. of n-butanol by the application of heat. When the resulting solution was allowed to stand at room temperature for 2 hours, 2.1 g. of the 1:1 inclusion complex of Compound D and 2-butyne-1,4-diol was obtained in the form of colorless prisms. This crystalline product had a melting point of 176°–178° C., and gave an infrared absorption spectrum as shown in FIG. 6.

When the product was heated to 200° C. under a reduced pressure of 25 mmHg, 0.13 g. of 2-butyne-1,4-diol was recovered.

EXAMPLE 7

2.0 g. of Compound D and 0.59 g. of 1,4-butanediol containing 30 wt.% of water were dissolved in 5 ml. of n-butanol by the application of heat. When the resulting solution was allowed to stand at room temperature for 2 hours, 1.99 g. of the 1:1 inclusion complex of Compound D and 1,4-butanediol precipitated in the form of colorless prisms melting at 163°–166° C. An infrared absorption spectrum of this crystalline product is shown in FIG. 6.

When 1.99 g. of the product was heated to 200° C. under a reduced pressure of 25 mmHg, 0.27 g. of 1,4-butandiol was obtained.

EXAMPLE 8

2.0 g. of Compound D and 0.57 g. of 2-butene-1,4-diol (a mixture of cis- and trans-isomers) containing 30 wt.% of water were dissolved in 5 ml. of n-butanol by the application of heat. When the resulting solution was allowed to stand at room temperature for 2 hours, 1.86 g. of the 1:1 inclusion complex of Compound D and trans-2-butene-11,4-diol precipitated in the form of colorless prisms melting at 161°–169° C. When this crystalline product was collected by filtration and heated to 200° C. under a reduced pressure of 25 mmHg, 0.28 g. of trans-2-butene-1,4-diol was obtained.

EXAMPLE 9

2.0 g. of Compound D and 0.20 g. of ethylene glycol containing 30 wt.% of water were dissolved in 3 ml. of n-butanol by the application of heat. When the resulting solution was allowed to stand at room temperature for 1 hour, 1.80 g. of the 2:1 inclusion complex of Compound D and ethylene glycol was obtained in the form of colorless needles. This crystalline product had no definite melting point. When the product was heated to 150° C. under a reduced pressure of 25 mmHg, 0.10 g. of ethylene glycol was recovered.

EXAMPLE 10

2.0 g. of Compound D and 0.34 g. of diethylene glycol containing 30 wt.% of water were dissolved in 3 ml. of n-butanol by the application of heat. When the resulting solution was allowed to stand at room temperature for 1 hour, 1.84 g. of the 2:1 inclusion complex of Compound D and diethylene glycol was obtained in the form of colorless prisms melting at 151°-155° C. When the crystalline product was collected by filtration and heated to 200° C. under a reduced pressure of 25 mmHg, 0.09 g. of diethylene glycol was obtained.

EXAMPLE 11

1.0 g. of Compound D and 0.7 g. of phenol were dissolved in 5 ml. of acetone, and the resulting solution was allowed to stand for 24 hours. Thus, there was obtained a yield of 1.2 g. (85%) of a complex consisting of the host (Compound D) and the guest (phenol) in a molar ratio of 1:2. This complex had a melting point of 135°-141° C.

EXAMPLE 12-14

The procedure of Example 11 was repeated except that 0.7 g. of o-methylphenol was used in place of the phenol. Thus, there was obtained a yield of 1.3 g. (87%) of the 1:2 complex of Compound D and o-methylphenol having a melting point of 118°-120° C.

In the same manner, m-methylphenol gave the 1:2 complex of Compound D and m-methylphnol having a melting point of 124°-127° C., and p-methylphenol gave the 1:2 complex of Compound D and p-methylphenol having a melting point of 78°-87° C.

EXAMPLE 15

1.0 g. of Compound D and 1.5 g. of picric acid were dissolved in 15 ml. of acetone, and the resulting solution was allowed to stand for 24 hours. Thus, there was obtained a yield of 1.8 g. (93%) of the 1:2 complex of Compound D and picric acid having a melting point of 137°-148° C.

EXAMPLE 16

Preparation of N,N,N',N'-tetracyclohexyl-phenylmalonamide (Compound E)

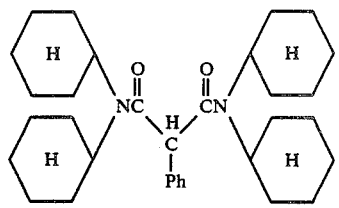

25 g. of diethyl phenylmalonate was heated with an excess (100 ml.) of dicyclohexylamine at a temperature ranging 160° C. to 180° C. for 20 hours. Thus, a dark-brown syrup resulted. 20 ml. of benzene was added and the resulting mixture was heated (boiled) with 5 g. of activated carbon to remove the color. After filtration, the benzene was removed and the excess of amine as well as any unreacted ester was distilled off at reduced pressure. The resulting crude solid was crystallized from acetone and recrystallized from dimethylformamide. Thus, there was obtained a yield of 20 g. of Compound E in the form of needles melting at 180°-182° C.

EXAMPLE 17

Preparation of N,N,N',N'-tetracyclohexyl-1,2-cyclohexanedicarboxamide (Compound F)

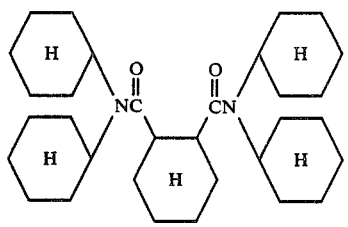

A 200 ml. round bottom flask was charged with 20 g. of 1,2-cyclohexanedicarboxylic acid and 49 g. of PCl₅. The flask was fitted with a condenser and CaCl₂ tube. A vigorous reaction took place. This, 1,2-cyclohexanedicarbonyl dichloride was obtained in the form of a colored thick liquid, which was not further purified.

A mixture of 31 ml. of dicyclohexylamine and 30 ml. of dry benzene was added to 8.0 g. of acid chloride in 10 ml. of dry benzene, followed by cooling in an ice bath with occasional shaking. The salt so formed was removed by filtration. Benzene was removed from the filtrate under reduced pressure and the product was crystallized from acetone. Thus, there was obtained a quantitative yield of Compound F in the form of crystals melting at 162°-186° C.

Compound F has good ability as a host and forms complexes with a variety of organic solvents. When treated with resorcinol in acetone or acetonitrile as solvent, it includes the guest as well as the solvent in 1:1:1 stoichiometry.

EXAMPLE 18

Preparation of
N,N,N',N'-tetracyclohexyl-cis-Δ⁴-cyclohexene-1,2-dicarboxamide (Compound G)

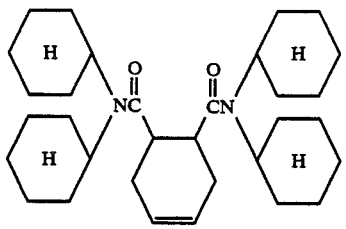

The corresponding acid chloride was prepared by heating 15 g. of cis-Δ⁴-tetrahydrophthalic anhydride with 22 g. of PCl₅, followed by the removal of POCl₃ under reduced pressure. Its yield was 50% (10.5 g.).

10 g. of the acid chloride thus obtained was treated with 40 ml. of dicyclohexylamine in 40 ml. of benzene at ice-bath temperature. This mixture was stirred at room temperature for 2 days. The resulting amine hydrochloride was removed by filtration, the benzene was distilled off and the residue was crystallized from acetone. The crystalline product thus obtained was found to be a complex of Compound G and acetone. When it was decomposed at reduced pressure, there was obtained a yield of 19 g. (80%) of Compound G having a melting point of 154°–157° C.

EXAMPLE 19

Preparation of
N,N,N',N'-tetracyclohexyl-2,6-pyridinedicarboxamide (Compound H)

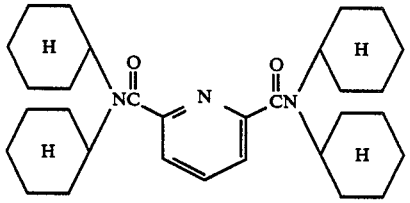

12 g. of commercial 2,6-pyridinedicarboxylic acid (dipicolinic acid), 12 g. was mixed with 30 g. of PCl₅ in a 200-ml. round bottom flask fitted with a condenser bearing anhydrous CaCl₂ tube. A vigorous reaction took place. The reaction mixture was heated for 1 hour and then allowed to stand overnight. After POCl₃ was removed under vacuum, the resulting acid chloride was crystallized from benzene. It had a melting point of 55°–57° C.

In a 250-ml. three-necked round bottom flask fitted with a condenser and a dropping funnel having a CaCl₂ tube was placed 39 ml. of dicyclohexylamine in 40 ml. of dry benzene. After the flask was immersed in an ice bath, 10 g. of 2,6-pyridinedicarbonyl dichloride in 20 ml. of dry benzene was added dropwise from the dropping funnel into the flask with shaking. The resulting reaction mixture was allowed to stand overnight. After the addition of 50 ml. of benzene, the reaction mixture was filtered through a Buchner funnel and the filtrate was concentrated by evaporating the benzene under reduced pressure. Upon standing overnight, prismatic crystals separated out. This crystalline product was found to be a complex of Compound H and benzene. When the complex was decomposed under reduced pressure, there was obtained a yield of 23 g. of Compound H in pure form. It had a melting point of 178°–180° C.

Compound H was found to be an effective host for many organic solvents. It could take up ethanol from ethanol-water mixtures (80:20, 70:30, 60:40 and 50:50), provided that the host was first dissolved in ethanol or ether. It did not form complex with acetone whenever crystallized from its solution. However, when crystallized from a dimethylsulfoxide-acetone, n-propanol-acetone or water-acetone mixture, Compound H always formed complexes with acetone.

EXAMPLE 20

Preparation of
N,N,N',N'-tetracyclohexyl-2,3-pyridinedicarboxamide (Compound I)

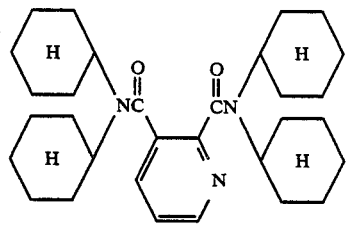

2,3-Pyridinedicarboxylic dichloride was prepared from 12 g. of the corresponding acid (quinolinic acid) and 30 g. of PCl₅ in the same manner as described for 2,6-pyridinecarboxylic dichloride in Example 19. The resulting acid chloride was a colored semi-solid material.

10 g. of the above acid chloride was treated with 39 ml. of dicyclohexylamine in dry benzene at low temperature (10° C.) and the resulting reaction mixture was allowed to stand overnight. After the addition of 50 ml. of benzene, the reaction mixture was filtered, and the filtrate was concentrated and allowed to stand. The precipitated colored crystalline product was recrystallized from acetone as a complex of Compound I and acetone. When this complex was decomposed by heating under reduced pressure, there was obtained a yield of 20 g. (80%) of Compound I in pure form. It had a melting point of 207°–208° C.

Compound I exhibits satisfactory host-guest-complex-forming property. Its ability to pick up ethanol from water is poor, though it can work where the ethanol concentration is 70% or more. It formed no complex with CH₃CN when treated with its solution, whereas it could include CH₃CN when treated with a mixture of 1,5-pentandiol and CH₃CN.

EXAMPLE 21

Preparation of
N,N,N',N'-tetracyclohexyl-2,5-pyridinedicarboxamide
(Compound J)

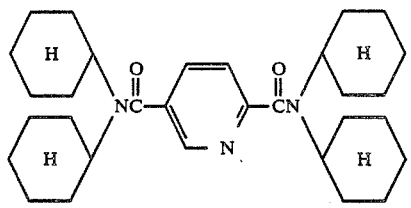

This amide was prepared from the corresponding acid in the same manner as described above in Example 20. Thus, there was obtained about the same yield of Compound J having a melting point of 209° C.

Compound J exhibited some host activity towards chloroform, benzene, pyridine, aniline, propargyl alcohol, cyclohexanone, γ-butyrolactone, α-methylnaphtalene and β-methylnaphtalene.

The aforesaid compounds of the present invention, when used as hosts, can form complexes with various guest compounds. Typical examples of such guest compounds are given in Table 1.

In the table, the numerals indicate the number of guest molecules taken up by each host molecule, the plus marks (+) indicate that the formation of a complex was noted, the minus marks (−) indicate that no complex was formed, and the blanks indicate that no test was made.

TABLE 1

| GUEST COMPOUND | HOST COMPOUND | | | | | | | | | |
|---|---|---|---|---|---|---|---|---|---|---|
| | A | B | C | D | E | F | G | H | I | J |
| Methanol | 1 | 2 | 4 | 2 | | − | 1 | 1 | 1 | |
| Ethanol | − | 1 | − | | | − | − | 1 | 1 | |
| n-Propanol | 1 | 1 | 3 | | | − | 1 | − | 1 | |
| i-Propanol | 1 | 1 | 3 | | | 2 | 1 | 1 | 1 | |
| n-Butanol | − | − | 1 | | | 1 | 1 | − | − | |
| s-Butanol | 2 | 1 | 1 | | | − | 1 | − | − | |
| i-Butanol | 1 | 1 | 1 | | | − | 1 | − | 1 | |
| t-Butanol | 1 | − | 2 | 2 | | 2 | 1 | 1 | 1 | |
| n-Pentanol | | − | + | | | | | | | |
| n-Hexanol | | − | ½ | | | | | | | |
| cis-3-Hexenol | | | | 1 | | | | | | |
| Allyl alcohol | | | | 2 | | | | | | |
| Propargyl alcohol | 1 | 1 | 3 | 2 | | − | − | 1 | 1 | + |
| Cyclohexanol | − | 1 | + | | | 2 | − | − | − | |
| 4-Methyl-cyclohexanol | | + | + | | | | | | | |
| n-Octanol | | − | + | | | | | | | |
| n-Decanol | − | − | 1 | | | | | | | |
| Ethylene glycol | ½ | 1 | − | ½ | | − | 1 | | | |
| Diethylene glycol | | − | − | ½ | | | | | ½ | |
| 1,3-Propanediol | ½ | 1 | | | | | | | | |
| 1,4-Butanediol | − | | | 1 | | | 1 | 1 | ½ | |
| 2-Butene-1,4-diol | | | | 1 | | | | | | |
| 2-Butyne-1,4-diol | | | | 2 | | | | | | |
| Phenol | 1 | 2 | 3 | 2 | | | | 1 | − | |
| o-Cresol | 2 | 2 | 1 | 2 | | − | − | 2 | − | |
| m-Cresol | 2 | 1 | 1 | 2 | | 2 | − | 2 | − | |
| p-Cresol | 2 | 2 | 3 | 2 | | − | − | 2 | 1 | |
| Resorcinol | 1 | | | 1 | | | | | | |
| α-Naphthol | | | | 2 | | | | | | |
| β-Naphthol | | | | 2 | | | | | | |
| Benzene | 1 | | 2 | | 2 | 1 | 1 | 1 | 1 | 1 |
| Toluene | | | 1 | | | | | | | |
| o-Xylene | | | 1 | | | | | | | |
| m-Xylene | | | 1 | | | | | | | |
| p-Xylene | | | 1 | | | | | | | |
| Bromobenzene | | | 1 | | | | | | | |
| Nitrobenzene | | | 2 | | | | | | | |
| Aniline | 1 | | 2 | 2 | 1 | 1 | 1 | 1 | 1 | |
| Ethyl benzoate | | 1 | 1 | | | | | | | |
| Benzoic acid | | 1 | 1 | | | − | − | 1 | 1 | − |
| Acetic acid | | | 1 | 4 | 2 | | | | | |

TABLE 1-continued

| GUEST COMPOUND | HOST COMPOUND | | | | | | | | | |
|---|---|---|---|---|---|---|---|---|---|---|
| | A | B | C | D | E | F | G | H | I | J |
| Glycolic acid | | − | + | 1 | | | | | | |
| Picric acid | | | | 2 | | | | | | |
| 3-Hydroxy-propionitrile | | | | 1 | | | | | | |
| Dimethyl sulfoxide | | − | − | | | | | | | |
| Dimethylformamide | 1 | 1 | − | | − | − | − | − | − | − |
| Dichloromethane | | 1 | 3 | | | | | | | |
| Chloroform | | 1 | 3 | | | | | | | + |
| Carbon tetrachloride | − | 1 | 3 | | 1 | 2 | 2 | − | 1 | − |
| Acetone | − | − | − | | − | − | − | − | 1 | − |
| Acetonirile | | | | | − | − | − | 1 | − | − |
| Tetrahydrofuran | ½ | ½ | 3 | | 1 | 1 | 1 | − | 1 | − |
| Cyclopentanone | 1 | | | | | | | | − | |
| Cyclohexanone | | | | | | − | − | − | | 1 |
| γ-Butyrolactone | 1 | | | | | − | − | − | | 2 |
| Benzaldehyde | | | | | − | | | | | |
| 1,4-Dioxane | 1 | ½ | + | | 1 | 1 | 1 | 1 | 1 | − |
| Pyridine | | 2 | 3 | | | | | | | + |
| Diethylamine | | 1 | − | | | | | | | |
| Naphthalene | | 1 | | | | | | | | |
| α-Methylnaphthalene | | 1 | 2 | | | | | | | + |
| β-Methylnaphthalene | | 1 | − | | | | | | | + |
| Indene | | 2 | | | | | | | | |

What is claimed is:

1. A compound selected from the group consisting of N-cyclohexyl-polycarboxamide compounds of the formula

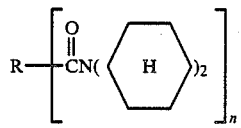

and derivatives thereof, where R is a benzene ring, an ethylidene group, a benzylidene group, a 1,2-cyclohexylene group, a 1,2-cyclohexenylene-4 group, or a 2,3-, 2,5- or 2,6-pyridinediyl group, and n is equal to 2, 3 or 4 when R is a benzene ring, and equal to 2 when R is one of the aforesaid groups excluding a benzene ring.

2. A compound as claimed in claim 1 wherein the N-cyclohexyl-polycarboxamide compound is N,N,N',N'-tetracyclohexyl-phthalamide.

3. A compound as claimed in claim 1 wherein the N-cyclohexyl-polycarboxamide compound is N,N,N',N',N'',N''-hexacyclohexyl-trimesamide.

4. A compound as claimed in claim 1 wherein the N-cyclohexyl-polycarboxamide compound is N,N,N',N',N'',N'',N''',N'''-octacyclohexyl-pyromellitamide.

5. A compound as claimed in claim 1 wherein the N-cyclohexyl-polycarboxamide compound is N,N,N',N'-tetracyclohexyl-fumaramide.

6. A compound as claimed in claim 1 wherein the N-cyclohexyl-polycarboxamide compound is N,N,N',N'-tetracyclohexyl-phenylmalonamide.

7. A compound as claimed in claim 1 wherein the N-cyclohexyl-polycarboxamide compound is N,N,N',N'-tetracyclohexyl-1,2-cyclohexanedicarboxamide.

8. A compound as claimed in claim 1 wherein the N-cyclohexyl-polycarboxamide compound is N,N,N',N'-tetracyclohexyl-cis-Δ⁴-cyclohexene-1,2-dicarboxamide.

9. A compound as claimed in claim 1 wherein the N-cyclohexyl-polycarboxamide compound is N,N,N',N'-tetracyclohexyl-2,6-pyridinedicarboxamide.

10. A compound as claimed in claim 1 wherein the N-cyclohexyl-polycarboxamide compound is N,N,N',N'-tetracyclohexyl-2,3-pyridinedicarboxamide.

11. A compound as claimed in claim 1 wherein the N-cyclohexyl-polycarboxamide compound is N,N,N',N'-tetracyclohexyl-2,5-pyridinedicarboxamide.

* * * * *